(12) United States Patent
Picaut

(10) Patent No.: US 12,276,066 B2
(45) Date of Patent: Apr. 15, 2025

(54) METHOD FOR PRODUCING A FINISHED LEATHER SUBSTITUTE

(71) Applicant: HERMES SELLIER, Paris (FR)

(72) Inventor: Lise Picaut, Montmorency (FR)

(73) Assignee: HERMES SELLIER, Paris (FR)

( * ) Notice: Subject to any disclaimer, the term of this patent is extended or adjusted under 35 U.S.C. 154(b) by 0 days.

(21) Appl. No.: 18/097,915

(22) Filed: Jan. 17, 2023

(65) Prior Publication Data

US 2023/0265606 A1    Aug. 24, 2023

(30) Foreign Application Priority Data

Jan. 17, 2022  (EP) .................................... 22305035

(51) Int. Cl.
*D06N 3/00*  (2006.01)
*D06N 3/04*  (2006.01)

(52) U.S. Cl.
CPC ............. *D06N 3/0002* (2013.01); *D06N 3/04* (2013.01); *D06N 2211/28* (2013.01)

(58) Field of Classification Search
CPC .... D06N 3/0002; D06N 3/04; D06N 2211/28; C12R 2001/645; C08L 5/08; C12N 1/14
See application file for complete search history.

(56) References Cited

U.S. PATENT DOCUMENTS

| | | | | |
|---|---|---|---|---|
| 2018/0014468 A1* | 1/2018 | Ross | .................. | C05F 9/04 |
| 2020/0392341 A1* | 12/2020 | Smith | .................. | C12N 1/14 |
| 2021/0010198 A1* | 1/2021 | Stewart | .................. | D06N 3/0015 |

FOREIGN PATENT DOCUMENTS

| | | | | |
|---|---|---|---|---|
| WO | WO-2007071323 A1 * | 6/2007 | ............... | C08F 8/00 |
| WO | 2018/014004 | 1/2018 | | |
| WO | 2020047458 | 3/2020 | | |
| WO | 2020/087033 | 4/2020 | | |
| WO | 2020/257320 | 12/2020 | | |
| WO | 2021245608 A1 | 12/2021 | | |

OTHER PUBLICATIONS

Jones et al., "Leather-like material biofabrication using fungi," Nature Sustainability, 4, 9-16 (Jan. 2021). (Year: 2021).*
Meyer et al., "Comparison of the Technical Performances of Leather, Artificial Leather, and Trendy Alternatives," Coatings 2021, 11, 226 (Feb. 13, 2021). (Year: 2021).*
Elkhateeb et al., "Fungi-derived leather (Mushroom leather)," MycoKing 1:1-9 (Nov. 18, 2022). (Year: 2022).*
European Search Report issued Jun. 21, 2022 in connection with European Application No. 22305035.
Sun et al., "Functionality of Surface Mycelium Interfaces in Wood Bonding," ACS Appl. Mater, Interfaces, 2020, 12, 57431-57440.
Office Action issued Nov. 22, 2024 in connection with Chinese Patent Application No. 202310079667.4 (including English Translation).

* cited by examiner

*Primary Examiner* — William P Fletcher, III

(74) *Attorney, Agent, or Firm* — Troutman Pepper Locke LLP

(57) ABSTRACT

A method for producing a finished leather substitute, finished leather substitutes obtainable by such method, and uses thereof are provided. Specifically, a method for producing a finished leather substitute is provided, comprising providing a sheet material grown from mycelium having a top surface layer and a bottom surface, and applying at least one finishing coating to the bottom surface only.

14 Claims, 3 Drawing Sheets

METHOD FOR PRODUCING A FINISHED LEATHER SUBSTITUTE

The invention relates to a method for producing a finished leather substitute, finished leather substitutes obtainable by such method, and uses thereof.

CROSS-REFERENCE TO RELATED APPLICATIONS

This application is based on European Application No. 22305035.2, filed Jan. 17, 2022, which is incorporated herein by reference in its entirety for all purposes.

BACKGROUND OF THE INVENTION

Leather is used in a vast variety of applications, including furniture upholstery, clothing, shoes, luggage, handbag and accessories, and automotive applications. Currently, skins of animals are used as raw materials for natural leather. Synthetic leather has been developed which is not made from animal skin or hide like genuine leather, but from natural and/or synthetic fibers, coated with a synthetic polymer or similar. Though there are a number of materials used, most synthetic leathers consist of a knitted polyester base with a polyurethane and polyvinyl chloride coating. Processing but also the life and the end of life of these microplastic, non biodegradable plastic-based products is still far from being environmentally friendly. Furthermore such synthetic leather lacks the quality, durability, and prestige of natural leather.

Therefore, current trends move towards the use of non-petroleum-based materials, especially vegetable sources. The fungal-based materials, in particular those of mycelium type, are natural materials, whether composite or not, and obtained by the growth of fungal materials. Their growth is controlled so as to obtain a wide variety of shape, size, density. Materials obtained from mycelium, such as, for example, those described in international patent application WO2018014004 (Mycoworks), US patent application 2015/0033620 or U.S. Pat. No. 9,485,917 (Ecovative Design) or international patent application WO2020237201 (Bolt threads) make it possible to manufacture materials in the form of thick sheets which can be used as a substitute for leather.

However, before they can be used as leather substitutes, these raw materials need to be treated, typically stabilized and plasticized, and ennobled. Ennobling of the material may involve coloring it, modifying its flexibility, mechanical properties, density, and also adding some coating or finishing on the surface of the material in order to improve color uniformity, water repellency, smooth touch.

SUMMARY OF THE INVENTION

The inventors have realized that finishing the top surface of the materials grown from mycelium as leather substitutes was yet not fully satisfying. They lacked homogeneity, some areas on the top surface were more dense, or more or less hydrophobic, or more or less porous, which led to a non-homogeneous adhesion of topcoats, coloring, and plasticization and lubrication of the surface. Furthermore the inventors have evidenced that the top surface did not let aqueous solutions penetrate, due to a high surface fibers density and a more hydrophobic nature.

The inventors then made the counter-intuitive decision to apply the finish coating to the bottom surface, and to use the finished bottom surface as the visible part of the leather substitute. In other words, the inventors flipped the material and finished the bottom surface only.

The invention thus provides a method for producing a finished leather substitute, which method comprises
 a) providing a sheet material grown from mycelium, which sheet material shows a top surface layer and a bottom surface layer that are defined in the sense of growth of the mycelium, from the bottom to the top;
 b) contacting the sheet material with an aqueous solution comprising lubricants;
 c) drying it;
 d) applying at least one finishing coating on the bottom surface only.

The finishing can be applied in one or in multiple coats, at the same time or successively. Another subject of the invention is the finished leather substitute obtainable by the method as defined herein.

Still another subject of the invention is the use of the finished leather substitute as a substitute for leather in the fashion, accessories, household's appliances and other furniture industries.

LEGENDS TO THE FIGURES

FIG. 1 is a schematic drawing that shows the growth of a mycelium, defining the top and bottom surface, as described in international patent application WO2018014004 from which the Figure was reproduced.

FIG. 2 is a schematic drawing of a method of the invention. The Top layer is the face in contact with the air and the Bottom one, closest to the nutrient medium during mycelium growth. The internal part is made of mycelium (A. left-hand) but can also incorporate another material such as a textile (B. right-hand), ensuring mechanical resistance to the whole. After processing, flipping and finishing the material, the resulting final outer part of the finished article is the lower part of the starting mycelium sheet material.

DETAILED DESCRIPTION OF THE INVENTION

Growth of the Mycelium

Filamentous fungi grow their bodies as an expanding and interconnected web of threadlike cells (called hyphae) directly within the food they are in the process of consuming as nutrients. Filamentous fungi have the natural tendency to join together smaller pieces of branching, colonial hyphae into a larger constituent whole, assembling and weaving strands and sheets of tissues called mycelium.

The mycelium used in the present invention may originate from any desired fungal inoculum, i.e. any desired amplifiable colony of a desired fungal strain. For instance the fungal species may be selected from the group consisting of ascomycetes, basidiomycetes, deuteromycetes, oomycetes, and zygomycetes, preferably from the fungal kingdom order Polyporales, the Family Ganodermataceae, with preference to the *Ganoderma lucidum, Ganoderma tsugae, Ganoderma applanatum, Ganoderma resinaceum, Ganoderma oregonense*. Other candidates include *Trametes versicolor, Trametes pubescens, Schizophyllum commune*, and *Polyporous squamosus*.

In a preferred embodiment, the mycelium is *Ganoderma* mycelium.

The sheet material grown from mycelium may be obtained by any method known in the art, e.g. using the method described in patent application WO2018014004 (Mycoworks).

As used herein, the term "sheet" refers to a layer of solid material having a generally flat or planar shape and a high ratio of surface area to thickness.

Figure 1:
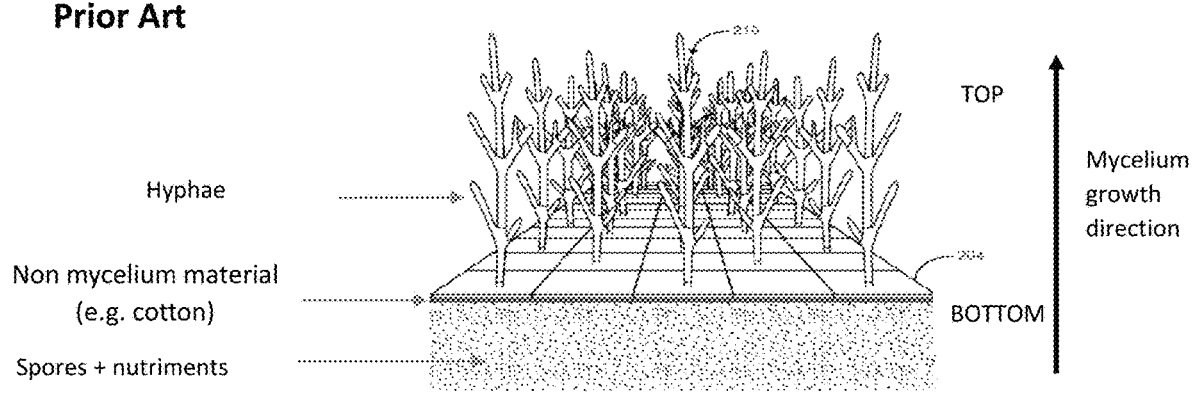

First fungal inoculum may be introduced into a nutritive substrate, which may comprise a mixture of discrete particles and nutrients, such as lignocellulosic waste, within an enclosure or prior to being introduced to the enclosure so as to provide an even distribution of the fungus throughout. The substrate is left to colonize. An intermediate layer may be established on an open surface of the colonized substrate to control the interaction of the forming fungal tissue structure with the substrate. In a particular example, cellulose-based materials, e.g. cotton or rayon, are often used as they are both biodegradable and a non-preferred food source for *Ganoderma*, meaning they maintain strength through the growth process in ways that lignin-bearing materials do not. The presence of a uniform intermediate material atop the substrate enables a consistent surface from which the fungal tissues may grow, supporting uniform expansion of the fungal hyphae into the environment. Live fungal hyphae grow from the substrate and through the intermediate layer. See FIG. 1.

In a particular embodiment, the fungal material may be periodically manipulated to direct growth in ways that confer desired characteristics, including density, evenness, and higher strength. The growth of fungal material can be directed, e.g. in predetermined patterns such as orthogonal structures, lattices and other two or three-dimensional structures.

The fungal tissues may be modified and directed during growth in order to achieve uniform characteristics across a surface, or be engineered to take on distinct local qualities through manipulation of growing tissue, or the addition of particles, fibers, meshes, fabrics, and other additives, armatures, and components.

The intermediate layer may be delaminated from the nutrient source out of which it has grown to terminate further growth of the material, or the fungal tissue layer may be delaminated from the intermediate layer, which is left in place and optionally reused.

In a particular embodiment, the sheet material grown from mycelium has been obtained by a method comprising the steps of:
a. providing a nutritive vehicle;
b. growing fungal tissue from said nutritive vehicle, the fungal tissue comprising fungal hyphae;
c. extending fungal tissue growth through a porous material defining an intermediate layer;
d. causing a portion of said fungal tissue extending through the porous material away from said nutritive vehicle to grow into an administrable space, wherein the fungal tissue within said space defines at least one successive fungal material layer;
e. directing a change in the composition or growth pattern of at least one of said fungal hyphae in at least one layer;
f. separating at least a portion of the fungal material from said nutritive vehicle; and
g. altering through physical or chemical means said portion of the fungal material.

The intermediate layer typically does not readily bind with said fungal tissue and provides uniform initial conditions of growth thereby achieving uniform growth of the fungal tissue. The porous material is preferably microperforated or woven.

After the growing fungal tissue is manipulated to direct a change in the growth pattern, the fungal material may be pulled off the intermediate layer thereby promoting a continuous growth of the fungal material.

In another embodiment, the material obtained by growth of the mycelium may a self-supporting material, such as the material obtained by the method described in U.S. Pat. No. 9,485,917 (Ecovative Design).

In that method, hyphae are grown through the substrate, with the net shape of the substrate bounded by the physical dimensions of the enclosure.

In next step, the substrate, now held tightly together by the mycelia network, is separated from the enclosure, and any internal enclosures or elements are separated away, as desired.

Composite Materials

In a particular embodiment, the sheet material grown from mycelium further comprises another material not grown from mycelium, optionally embedded within the mycelium.

Materials may be incorporated into the growing fungal tissue while the fungal material is still viable, to direct growth and/or produce composite materials. In one embodiment, cellulose-based, synthetic or other organic fibers including various textile forms (e.g. woven, knit, fulled, felted) of preferred lengths and structural characteristics are deposited on the exposed surface of the growing fungal tissue, allowing for the growth of a composite material. The composition and organization of the composite fibers enables the fungal tissue to be engineered, enhancing mechanical properties of the overall material including tensile and compressive strength.

In an alternate embodiment, fungal tissue can be grown through 2D and 3D matrices and objects of various materials to create composites with desired characteristics and qualities. This added layer of material may be composed of any material that fungal cells can grow through (pore size larger than 1 micron). These layers may be pressed onto or near the surface of the growing cells or otherwise impressed upon its surface, or placed between two or more layers of growing fungal material, such that these reinforcement layers are then incorporated into the fungal tissue. The material not grown from mycelium preferably includes cotton, silk, linen, polyester, polyamide, wool, nylon, Dyneema®, cellulose, or any regenerated cellulose fiber (also called "rayon") including viscose, modal, and lyocell (Tencell/Lenzing AG), or any combination thereof.

The Top and Bottom Surface Layers

A sheet material grown from mycelium is typically not homogenous, and shows a structural polarity, with a top surface layer that is more hydrophobic than the bottom layer.

The top surface layer may be defined as comprising more fungal hyphae tips compared to the bottom surface layer and/or as the surface that is in contact with air (or gas) during the growth of the mycelium.

Generally, the top surface layer and the bottom surface layer are defined in the sense of growth of the mycelium, from the bottom to the top.

The top surface layer and the bottom surface layer exhibit different structural properties. The top surface layer is typically less porous and more hydrophobic compared to the bottom surface layer.

It should thus be understood that the sheet material grown from mycelium, used as the starting material in the present invention, is not a material obtained nor obtainable by a process comprising crushing the mycelium and transforming into a paste, optionally with the addition of a polymer. Such material would not show a structural polarity, with a top surface layer that is more hydrophobic than the bottom layer.

Lubricating

The method of the invention comprises a step b) of contacting the sheet material with an aqueous solution comprising lubricants. This step is also called lubricating or fatliquoring step, as it introduces oil into the material.

This contacting step may comprise soaking the material with the solution, e.g. by plunging it in a drum, a washing machine, a steady tub or other suitable means of treatment.

In a preferred embodiment, the aqueous solution comprising lubricants contains fatliquors and emulsifying agents.

Fatliquors may typically include various types of oils such as mineral, synthetic, animal and plant-based oils or combinations and mixtures thereof. Oils based on animal fats may be for example fish oil, wool fat, beewax, or lard oil. Oils based on plant-based fats may be for example castor oil, coconut oil, cotton oil, olive oil, colza oil, linseed oil. For example oils that are based on synthetic oils may be derived from modified or synthetic fatty acid or fatty alcohol or modified vegetable or animal oils. These fatliquors are preferably obtained by sulfating, sulfiting or formation of sulfonic acids of said oils so that they are soluble or emulsifiable in water.

Other plasticizers and humectants may be used that are well-known in the art, such that the micro-droplets of oil may penetrate the material. Various fatliquors contain emulsified oil in water with the addition of other compounds such as ionic and non-ionic emulsifying agents, surfactants, soap, and sulfate.

Plasticizing and Stabilizing

In a preferred embodiment, step b) of the method further comprises plasticizing and/or stabilizing the sheet. The steps of plasticizing and stabilizing can be carried out simultaneously or successively to the lubricating.

In a preferred embodiment, plasticizing and/or stabilizing may be performed by contacting the sheet with at least one polyol and/or fatliquor. optionally in combination with at least one polycarboxylic acid.

Examples of plasticizing agents include glycerol and esters thereof, sorbitol, polyethylene glycol, polypropylene glycol, propanediol, citric acid, oleic acid, oleic acid polyols and esters thereof, epoxidized triglyceride vegetable oils, castor oil, pentaerythritol, fatty acid esters, carboxylic ester-based plasticizers, trimellitates, adipates, sebacates, maleates, biological plasticizers, and combinations thereof.

Preferably the sheet may be contacted with glycerol, preferably in combination with citric acid (preferably in water).

Said agents may be added in the drum or in any apparatus where the material is plunged. Massaging the sheet for complete penetration may further be advantageous.

Tanning and Dyeing

In a preferred embodiment, step b) of the method further comprises contacting the sheet material with tannins, preferably wherein the aqueous solution comprising lubricants further comprises tannins. Preferred tannins are condensed tannins, hydrolysable tannins and/or synthetic tannins.

As used herein, the term "tannin" refers generally to any molecule that forms strong bonds with protein structures. The most commonly used types of tannins are vegetable tannins, i.e. tannins extracted from trees and plants, and chromium tannins such as chromium (III) sulfate. Other examples of tannins include modified naturally derived polymers, biopolymers, and salts of metals other than chromium, e.g. aluminum such as aluminium silicate (sodium aluminum silicate, potassium aluminum silicate, etc.) or alun. Synthetic tannins can also be used such as those obtained by condensation of sulfonated aromatic compounds and/or unsulfonated aromatic compounds with formaldehyde and/or urea.

Various dyes may be used to impart color to the sheet material such as acid dyes, direct dyes, disperse dyes, sulfur dyes, synthetic dyes, reactive dyes, pigments (e.g. iron oxide black, titane dioxide and cobalt blue) and natural dyes. In some embodiments, the material is submerged in an alkaline solution to facilitate dye uptake and penetration into the material prior to application of a dye solution. In some embodiments, the material is pre-soaked in ammonium chloride, ammonium hydroxide, and/or formic acid prior to application of a dye solution to facilitate dye uptake and penetration into the material, preferably before fixing the dyes by lowering the pH. In some embodiments, tannins may be added to the dye solution.

In various embodiments, a plasticization agent is added after or during the addition of the dye. In various embodiments, the plasticization agent may be added with the dye solution.

In various embodiments, the material may be subject to mechanical working or agitation while the dye solution is being applied in order to facilitate dye uptake and penetration into the material.

Drying

The sheet material that has been wetted with the aqueous solution comprising lubricants, and optionally subjected to various treatments with plasticizing and/or stabilizing agents, tannins, and/or dyes, may then be typically cured by cross-linking, typically by heating at 50-100° C., preferably 70-80° C., preferably for 10 to 60 min.

The drying step c) of the method then involves leaving the material several days at room temperature or in a ventilated oven (at about 20-40° C.) or in a tannery dryer tunnel.

In a preferred embodiment, the polymerization between the polycarboxylic acid (e.g. citric acid), the polyol (e.g. glycerol) and the mycelium material induces a stabilization of the smooth appearance of the surface as well as a strengthening of the overall material. Moreover, it allows the material to keep suppleness after drying.

Finishing

The method of the invention comprises a step d) of applying at least one finishing coating on the dried material.

The finishing process may use surface coating techniques such as padding, spraying or roller coating. Preferably, the deposit of this finishing coating is carried out by roller coating so as to lay down and compact the mycelium fibers, while lining the surface.

Mechanical processes such as buffing, staking and embossing, may be used as well.

One or more finishing coating layers may be applied.

The finishing coating is typically applied by contacting aqueous solution(s) containing a polymer emulsion, cross-linkers and optionally pigment(s) and/or filler(s) on the dried sheet. In a preferred embodiment, several solutions are applied.

The finishing coating may comprise at least one monomer, and potentially at least one catalyst, the process further comprising a step of polymerizing said monomer(s). In another embodiment, the finishing coating may comprise at least one polymer, at least one crosslinking agent, and potentially at least one catalyst, and the process further comprises a step of crosslinking said polymer(s).

In a preferred embodiment, a first aqueous layer that is called a primer coat, is applied to promote adhesion. The primer may comprise a dispersion of alcohol and polymer. After drying of the primer, a subsequent coat is applied, which may contain emulsion of several resins and a crosslinker. At this stage, coloring agents, pigments or fillers may be added in this mixture in order to bring or adjust color of the final material, namely the finished leather substitute. For example, the polymer emulsion may comprise an emulsion of anionic, cationic or neutral polyurethane or acrylate, in aqueous medium and/or in the presence of cationic or nonionic anionic surfactants and/or in the presence of an alcoholic organic solvent.

Finally, one or more layers called top coat are typically applied, to protect the material from abrasion and discoloration, and also to give its final haptics and aesthetics to the finished leather substitute. It may be composed of a mixture of polymers, silicone agents and crosslinker. Optionally, crosslinking agents, e.g. polycarbodiimide or polyisocyanate or polyaziridine, can be added to stiffen the deposited layers and ensure better mechanical resistance.

If necessary, a surfacing, a texturing or a polishing step can be carried out in order to give a texture of the material or smoothen the surface.

In a particular embodiment, the finishing step d) may comprise incorporating fillers of natural origin such as microcrystalline cellulose or cellulose nanofibrils and/or grounded seashell.

In another preferred embodiment the finishing step d) comprises applying an emulsion of natural polymers, e.g. casein, albumin or other proteins, or synthetic polymers e.g. polyurethane and polyacrylate.

Typically, a 24 h time is advantageous for the finishing to stabilize and dry before proceeding to the next step.

Finished Leather Substitutes

The product obtainable by the method herein described is a finished leather substitute. It can be used as a substitute for leather in the fashion, accessories, household's appliances and other furniture industries.

It may be used especially for manufacturing bags, shoes, watch straps, belts or wallets.

The Figures and Example illustrate the invention without limiting its scope.

EXAMPLE

The mycelium sheet material was obtained as described in international patent application WO2018014004 (Mycoworks).

Figure 3A:
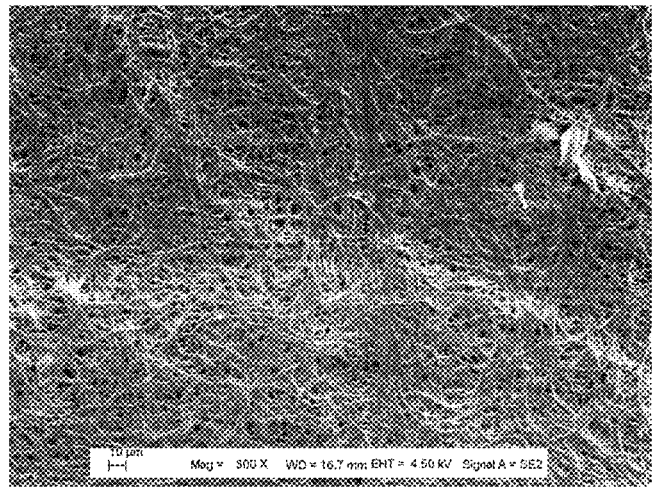
FIG. 3A and FIG. 3B are SEM photographs (scanning electron microscope) of the top surface (3A) and of the bottom surface (3B).
Figure 3B:
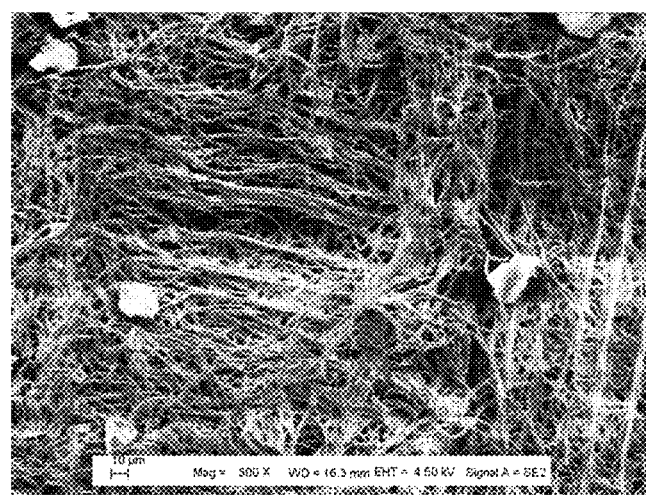

FIGS. 3A and 3B are respectively SEM images of the top surface and bottom surfaces, showing the difference in terms of structure and porosity. The top surface is less porous and mycelium hypheas are compacted and fused while the bottom surface is more porous and less compact. Absorption time of water droplets is measured on a contact angle goniometer apparatus. The water droplet absorption time are 27 s and 1.5 s for the top face and bottom face respectively while the contact angle at t=0 s are 73° and 43° for the top face and the bottom face respectively. These results confirm an easier penetration of water and higher hydrophily of the bottom face compared to the top face.

Figure 2:
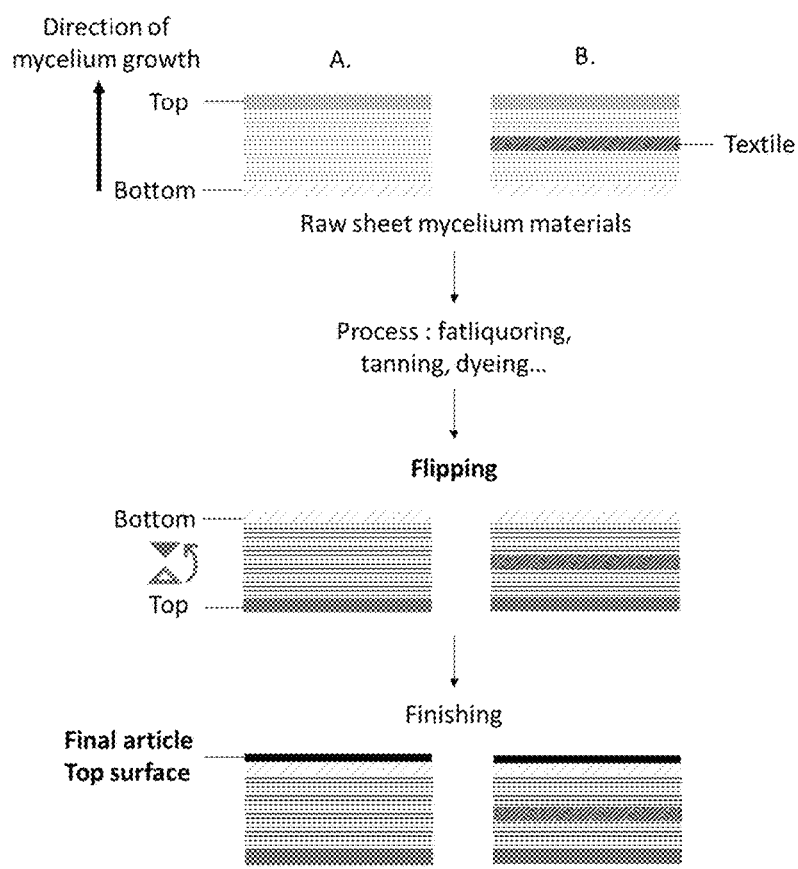

The mycelium sheet is then subjected to the following treatment, also shown on FIG. 2:

Soaking: the mycelium sheet is first soaked in a water-based solution at room temperature, static conditions.

Stabilization/lubrication: the material is then stabilized in a drum, by using a bath at 40 to 60° C. composed of a mix of water, glycerin, vegetable tanning agents, fatliquors, dyes prior fixation in acidic conditions Plasticization: the material is plasticized by adding glycerol and citric acid in water and massaging at room temperature in order to achieve a complete and uniform penetration of this mixture.

Drying: the material is then cross-linked by heating at 50 to 80° C. for 5 to 120 min and finally dried at 25° C. to 40° C.

Finishing: A finishing coating is then applied on the bottom surface layer only, by spraying various aqueous solutions containing a polymer emulsion comprising: water, filler agent (colloidal resins), polymer and wax emulsion, as well as a softening agent composed of oils and a penetrating solution comprising wetting agents.

Figure 4:
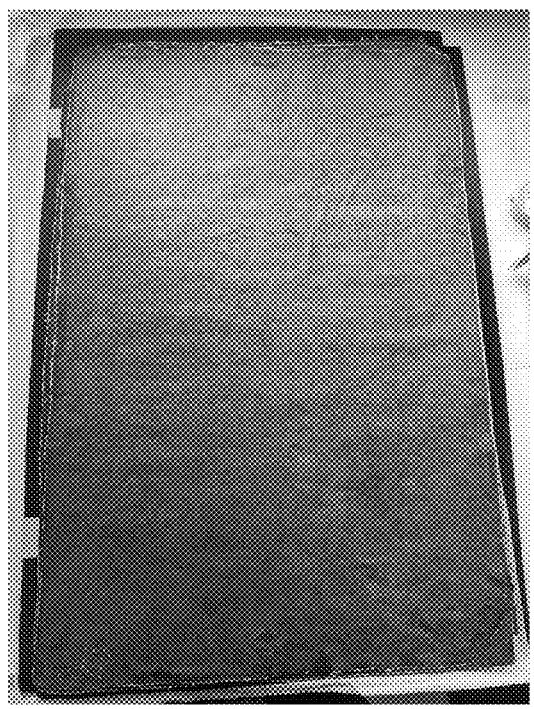
FIG. 4 is a picture of a resulting mycelium sheet material (Bottom) processed as described in FIG. 2.

The finished product (see FIG. 4) shows excellent properties as a leather substitute, especially in term of resistance to abrasion and to flexion. Furthermore it is not affected by weather changes nor ultraviolets.

The invention claimed is:

1. A method for producing a finished leather substitute, which method comprises:
    a) providing a sheet material grown from mycelium, which sheet material shows a top surface layer and a bottom surface layer that are defined in the sense of growth of the mycelium, from the bottom to the top;
    b) contacting the sheet material with an aqueous solution comprising lubricants;
    c) drying it;
    d) applying at least one finishing coating on the bottom surface only, wherein the finishing coating is applied by contacting an aqueous solution on the bottom surface of the dried sheet, wherein said aqueous solution in step d) contains i) a polymer or ii) a monomer and a catalyst.

2. The method of claim 1, wherein the finishing coating is applied by contacting an aqueous solution containing a polymer emulsion and optionally pigment(s) and/or filler(s) on the bottom surface of the dried sheet.

3. The method of claim 2, wherein the finishing coating is applied by spraying an aqueous solution containing a polymer emulsion and optionally pigment(s) and/or filler(s) on the bottom surface of the dried sheet.

4. The method of claim 1, wherein step b) further comprises contacting the sheet material with tannins.

5. The method of claim 4, wherein the aqueous solution comprising lubricants further comprises tannins.

6. The method of claim 1, wherein step b) further comprises plasticizing and/or stabilizing the sheet.

7. The method of claim 6, wherein plasticizing and/or stabilizing the sheet is performed by contacting the sheet with at least one polyol and/or fatliquor, optionally in combination with at least one polycarboxylic acid.

8. The method of claim 7, wherein the sheet is tanned.

9. The method of claim 1, wherein the finishing coating comprises at least one monomer and at least one catalyst and wherein the process further comprises a step of polymerizing said monomer(s).

10. The method of claim 1, wherein the finishing coating comprises at least one polymer, at least one crosslinking agent, and at least one catalyst and wherein the process further comprises a step of crosslinking said polymer(s).

11. The method of claim 1, wherein the mycelium is *Ganoderma* mycelium.

12. A finished leather substitute obtainable by a method which comprises:
   providing a sheet material grown from mycelium, which sheet material shows a top surface layer and a bottom surface layer that are defined in the sense of growth of the mycelium, from the bottom to the top;
   contacting the sheet material with an aqueous solution comprising lubricants;
   drying it;
   applying at least one finishing coating on the bottom surface only, wherein the finishing coating is applied by contacting an aqueous solution on the bottom surface of the dried sheet, wherein said aqueous solution in step d) contains i) a polymer or ii) a monomer and a catalyst.

13. A method for manufacturing an item in the fashion, accessories, household's appliances or furniture industries, which method comprises utilizing the finished leather substitute of claim 12 as a substitute for leather.

14. The method of claim 13, wherein the item is selected from the group consisting of a bag, shoes, a watch strap, a belt and a wallet.

* * * * *